US010172363B2

United States Patent
Wakefield

(10) Patent No.: US 10,172,363 B2
(45) Date of Patent: Jan. 8, 2019

(54) CONTROL OF ARTHROPOD INFESTATION

(71) Applicant: Exosect Limited, Winchester, Hants (GB)

(72) Inventor: Maureen Elizabeth Wakefield, York (GB)

(73) Assignee: Exosect Limited, Winchester, Hampshire (GB)

( * ) Notice: Subject to any disclaimer, the term of this patent is extended or adjusted under 35 U.S.C. 154(b) by 0 days.

(21) Appl. No.: 15/305,019

(22) PCT Filed: Jun. 11, 2015

(86) PCT No.: PCT/GB2015/000170
§ 371 (c)(1),
(2) Date: Oct. 18, 2016

(87) PCT Pub. No.: WO2015/189542
PCT Pub. Date: Dec. 17, 2015

(65) Prior Publication Data
US 2017/0156344 A1    Jun. 8, 2017

(30) Foreign Application Priority Data
Jun. 13, 2014    (GB) .................. 1410677.7

(51) Int. Cl.
*A01N 63/04*    (2006.01)
*A01N 25/12*    (2006.01)
*A01N 59/00*    (2006.01)
*A01N 65/40*    (2009.01)

(52) U.S. Cl.
CPC ............. *A01N 63/04* (2013.01); *A01N 25/12* (2013.01); *A01N 59/00* (2013.01); *A01N 65/40* (2013.01)

(58) Field of Classification Search
None
See application file for complete search history.

(56) References Cited

U.S. PATENT DOCUMENTS

2009/0060880 A1    3/2009    Meikle et al.

FOREIGN PATENT DOCUMENTS

| CN | 102687731 A | 9/2012 |
|---|---|---|
| WO | 97/12516 A1 | 4/1997 |
| WO | 2011/157983 A1 | 12/2011 |

OTHER PUBLICATIONS

Mascarin et al. World J Microbial Biotechnol (2016) 32:177, pp. 1-26.*
Jeffrey C. Lord et al., "Desiccant Dusts Synergize the Effect of *Beauveria bassiana* (Hyphomycetes: Moniliales) on Stored-Grain Beetles", Journal of Economic Entomology, Apr. 1, 2001, pp. 367-372, vol. 94, No. 2, XP001526581.
Waseem Akbar et al., "Diatomaceous Earth Increases the Efficacy of *Beauveria bassiana* Against *Tribolium castaneum* Larvae and Increases Conidia Attachment", Journal of Economic Entomology, Apr. 1, 2004, pp. 273-280, vol. 97, No. 1, XP001526582.
C.G. Athanassiou et al., "Insecticidal effect of *Beauveria bassiana* (Balsamo) Vuillemin (Ascomycota: Hypocreales) in combination with three diatomaceous earth formulations against *Sitophilus granarius* (L.) (Cleopatra: Curculionidae)", Biological Control, Feb. 6, 2007, pp. 411-416, vol. 40, No. 3, XP005873575.
P. Golob, "Current Status and Future Perspectives for Inert Dusts for Control of Stored Product Insects", Journal of Stored Products Research, Jan. 1, 1997, pp. 69-79, vol. 33, No. 1, XP055214128.
William G. Meikle et al., "Impact of two treatments of a formulation of *Beauveria bassiana* (Deuteromycota: Hyphomycetes) conidia on *Varroa* mites (Acari: Varroidae) and on honeybee (Hymenoptera: Apidae) colony health", Exp. Appl. Acarol., 2008, pp. 105-117, vol. 46.
British Search and Examination Report for GB1410677.7 dated Dec. 30, 2014.
International Search Report for PCT/GB2015/000170 dated Sep. 29, 2015.
Written Opinion for PCT/GB2015/000170 dated Sep. 29, 2015.
International Preliminary Report on Patentability for PCT/GB2015/000170 dated Jun. 6, 2016.

* cited by examiner

*Primary Examiner* — Oluwatosin A Ogunbiyi
(74) *Attorney, Agent, or Firm* — Sughrue Mion, PLLC

(57) ABSTRACT

A dry powder formulation comprising spores of an entomopathogenic fungus that has activity against arthropods that infest dry commodity storage areas, wherein the spores are present in an amount of 2 to 5% w/w of the formulation; particles of an industrial mineral in an amount of 80 to 88% w/w of the formulation and having a volume mean diameter of ≥5 μm; and electret particles in an amount of 10 to 15% w/w of the formulation, and uses thereof.

17 Claims, No Drawings

CONTROL OF ARTHROPOD INFESTATION

CROSS REFERENCE TO RELATED APPLICATIONS

This application is a National Stage of International Application No. PCT/GB2015/000170 filed Jun. 11, 2015, claiming priority based on British Patent Application No. 1410677.7 filed Jun. 13, 2014, the contents of all of which are incorporated herein by reference in their entirety.

The present invention relates to a method of controlling arthropod infestation, formulations for treating arthropod infestation and uses thereof. In particular, the invention relates to methods of controlling arthropod infestation in dry commodity storage areas, methods for the application of formulations in dry powder form to arthropods, dry powder formulations comprising biological agents, electret particles, and industrial earth particles, and methods of producing such formulations, and uses thereof.

Dried commodity storage areas, such as grain silos and grain bins where grain is stored immediately after harvest or prior to processing attract arthropods such as mites and beetles, particularly beetles. Other dried commodity storage areas include warehouses, supermarket storage facilities, ship holds, freight containers such as boxes, crates and containers associated with and/or on trains, ships, aeroplanes, and road transport vehicles. For the purposes of the present invention, the terms 'dried commodity' and 'dried commodities' are used interchangeably and encompass dried commodities including whole grains for sowing or whole grains for use as food and/or in the making of processed foods, and storage sites for timber and products made from timber. Whole grains include those such as wheat, rice, barley and corn (often referred to as maize), pulses, beans, lentils and products derived from or made with dried commodities. Such dried commodity products also include processed foods such as pasta, grain flours, couscous, cereals, dried herbs, breakfast cereals, domestic livestock feed, for example for pigs, cows, sheep and horses, semolinas, breads, nuts (ground, flaked and/or whole nuts), snacking food, such as sweet and savoury items including biscuits, potato crisps, vegetable crisps, pretzels, cheese biscuits, dried wafers, and the like. Timber includes lumber, planking, articles made of timber such as roof scaffolding for buildings, paneling, doors and door frames, lintels, skirting board, hardboards, plywoods, furniture and the like. Arthropods such as insects, for example grain storage beetles, wood beetles and moths, feed on dried commodities and are a major cause of economic losses to farmers and the food and timber utilising industries.

When dried commodities are removed from dried commodity storage areas, many arthropods are left behind, inhabiting cracks and crevices in walls, floors and other support structures such as pillars and/or shelving. Conventional procedures for controlling arthropod infestations that rely on the use of chemicals applied as wet formulations to empty dried commodity storage areas are effective insofar as they kill arthropods that come into contact with the applied chemical. However, wet chemical formulations typically do not get into cracks and crevices inhabited by populations of arthropods. Such populations survive the application of chemicals that are applied to the surfaces of the surrounding environment and are thus free to infest new shipments of dried commodity that are deposited in the storage area, and so the cycle of commodity infestation with concurrent economic losses is repeated.

Other methods of treating dried commodity storage areas rely on the application of relatively high levels of arthropodicidal chemicals in dry powder form. However, the effectiveness of such treatments diminishes over time.

Biological agents have been used in the prior art in attempts to control infestations of various kinds of arthropods in various settings. In particular, certain strains of entomopathogenic fungi such as *Beauveria bassiana*, *Paecilomyces fumosoroseus* and *Lecanicillium* spp. have found use in the control of certain arthropods. Although entomopathogenic fungi are clearly seen as candidates for controlling infestations of arthropods, it is also apparent that most strains of entomopathogenic fungi are unsuitable as candidates for the control of arthropod infestations in the myriad of so-called dry commodity storage environments in which the effective use of strains of fungus would be desirable. Often, it has been shown that apparently suitable candidate strains of fungus are unable to tolerate the environmental extremes that often exist in man-made environments, such as dried commodity storage areas or other environments in which dried commodity foodstuffs as outlined above may be placed.

A problem in using biological agents such as candidate strains of entomopathogenic fungus which may be discovered in one country and proposed for use in a setting in a different country is that such strains may not perform well in the new setting because they are unable to tolerate the extremes of conditions that prevail in the environment in the country in which they are to be used. In addition, regulatory constraints may be so arduous as to make the importation of a likely candidate strain unfeasible and this may be coupled with doubts about being able to prove its likely effectiveness in an exotic environment.

U.S. Pat. No. 4,925,663 describes the use of inter alia a dry powder formulation comprising powdered rice, and a certain strain of a fungus, *Beauveria bassiana*, which has a particular virulence against fire ants, when used in an open environment.

Meikle et al (2007) J. Econ. Entomol. 100:pp 1-10 describes the use of carnauba wax as a carrier of *Beauveria bassiana* spores (strain Bb05002 that is indigenous to France) in beehives to control *varroa* mites. The environment within the hive is reported as having a relative humidity (RH) of from 40% to 50%, apparently at temperatures from 33° C. to 36° C. It appears that the ambient environment within the beehive is not subject to wide extremes of RH and temperature inter alia because the bees actively regulate the temperature within.

WO 2006/121350 describes the provision of certain biologically pure cultures of strains of entomopathogenic fungi, such as *Beauveria bassiana* for controlling phytopathogenic insects for use against *Thysanoptera* (thrips), *Hemiptera* (white fly) and others. The compositions described therein appear to be applied to plants in the field as a wet spray. WO 2011/157983 describes the provision of a strain of *Beauveria bassiana* that is useful in controlling the infestation of inter alia grain storage areas by employing a dry composition consisting of a wax in particulate form which carries spores or conidia to the target site. The described composition does not contain mention of the use of specified dry weight percentages of industrial minerals, electret particles and entomopathogen in the compositions claimed therein.

An advantage of formulations of the invention is that the effect of the mineral earth component, electret particle component and entomopathogen component appears to be synergistic and provides significantly better control over dried commodity infesting arthropods than the effect of each separate component when added together. Synergy is evident from the accompanying examples.

A further advantage of compositions of the present invention is that they are cheaper to manufacture than compositions of the prior art. Furthermore, compositions of the invention do not lead to a build-up of toxic residues on storage sites, or indeed, in dry commodities that may be stored and/or treated on site.

It is an object of the present invention to overcome or at least reduce the drawbacks of conventional methods of treating dry commodity storage areas for arthropod infestation. This and other objects will become apparent from the following description and examples.

According to the present invention there is provided a dry powder formulation comprising:
i) spores of an entomopathogenic fungus that has activity against arthropods that infest dry commodity storage areas, wherein the spores are present in an amount of 2 to 5% w/w of the formulation;
ii) particles of an industrial mineral in an amount of 80 to 88% w/w of the formulation; and having a volume mean diameter of ≥5 μm; and
iii) electret particles in an amount of 10 to 15% w/w of the formulation.

Preferably, the spores are present in an amount of 2-4.5% w/w, the particles of industrial material are present in an amount of 82.5 to 87% w/w, and the electret particles are present in an amount of 11 to 13% w/w of the dry powder formulation of the invention. An example of a composition of the dry formulation of the invention is one where the spores are present in 2.12 to 4.167% w/w, particles of industrial material are present in 83.3 to 85.1% w/w and electret particles are present in 12.5 to 12.80% w/w.

Formulations of the invention contain at least $1 \times 10^9$ CFU/gram dry weight, preferably the spores are present in an amount of at least $1 \times 10^{10}$ CFU/gram dry weight or in an amount of at least $1 \times 10^{11}$ CFU/gram dry weight. It is to be understood that the terms 'conidia', 'spore' and 'CFU' (standing for colony forming unit) can be used interchangeably depending on context and relate to the same thing, that is to say, viable spores, viable conidia or viable CFUs. The CFU is frequently referred to values displayed as orders of magnitude of viable CFUs, such as from $1 \times 10^8$ to $1 \times 10^{11}$ or higher. The skilled addressee will appreciate that in such orders of magnitude the viability of CFUs will typically lie in the range of 80% to 99% or even 100%.

Electret particles of use in the invention typically have a volume mean diameter of ≥10 μm, preferably from 10 to 40 μm, and most preferably from 10 to 30 μm. It is thought that the size of the electret particles should be at about 10 μm or more to minimise potential negative respiratory effects to workers.

The particles of industrial mineral are preferably of a volume mean diameter of ≥5 μm or more in size, such as 10 μm. It is thought that the size of the mineral earth particles plays a role in inhibiting respiration in arthropods that come into contact with them. The industrial mineral may be selected from any industrial mineral capable of being used in the present invention, such as clays, diatomaceous earth, sand, gravel, diatomite, kaolin, bentonite, silica, barite, gypsum, montmorillonite, and talc or a mixture of two or more thereof. Preferably, the industrial mineral is selected from kaolin, talc and bentonite or a mixture of two or more thereof. Most preferably the industrial mineral is selected from kaolin and talc or a mixture thereof.

The spores or conidia of entomopathogenic fungus of use in the invention may be selected from species such as *Beauveria bassiana* spp., *Paecilomyces fumosoroseus* spp., and *Lecanicillium* spp. Preferably, the entomopathogenic fungus is selected from *Beauveria bassiana* species that are capable of germinating on and penetrating the cuticles of dried commodity storage area infesting arthropods in a dried commodity storage area as defined herein. Preferred entomopathogenic fungus strains for acquiring spores or conidia of use in formulations and compositions of the invention include those selected from the species *Beauveria bassiana*. A suitable strain of *Beauveria bassiana* for use in providing spores or conidia of utility in the invention is the strain deposited under the Budapest Treaty, IMI 398548, deposited at the Centre for Agriculture and Biosciences International (CABI), Bakeham Lane, Egham, Surrey, TW20 9TY, UK on 11 May 2010. This deposit is described in PCT publication WO 2011/157983 in the paragraph bridging pages 8 and 9.

Formulations of the invention are also used to provide a covering or layer to dry commodity storage surfaces of at least $1 \times 10^9$ conidia/m², preferably from $1 \times 10^9$ to $1 \times 10^{11}$ conidia/m². For the purposes of the present invention and in line with what is stated hereinabove 'spores' 'CFUs' and 'conidia' are used interchangeably unless context demands otherwise. Thus, the numerical values for CFU/m², spores/m² and conidia/m² mean the same thing, for example $1 \times 10^9$ spores/m² means the same thing as $1 \times 10^9$ CFU/m² and $1 \times 10^9$ conidia/m².

The formulations of the invention may also contain suitable excipients commonly employed in the art such as flow agents or anti-caking agents selected from sodium bicarbonate, sodium ferrocyanide, potassium ferrocyanide, calcium ferrocyanide, bone phosphate, sodium silicate, silicon dioxide, calcium silicate, magnesium trisilicate, sodium aluminosilicate, potassium aluminium silicate, calcium aluminosilicate, stearic acid, polydimethylsiloxane and the like.

Additionally, formulations of the invention may contain other components such as additives selected from UV blockers such as beta-carotene or p-aminobenzoic acid, colouring agents such as optical brighteners and commercially available colouring agents, such as food colouring agents, plasticisers such as glycerine or soy oil, antimicrobials such as potassium sorbate, nitrates, nitrites, propylene oxide and the like, antioxidants such as vitamin E, butylated hydroxyl anisole (BHA), butylated hydroxytoluene (BHT), and other antioxidants that may be present, or mixtures thereof. The skilled artisan will appreciate that the selection of such commonly included additives will be made depending on end purpose, and perceived need.

Naturally, the skilled addressee will also appreciate that formulations of the invention may also be applied to dried commodity masses and admixed therein thus conferring protection against arthropod infestation to the dried commodity per se while in storage. The man skilled in the art will also appreciate that dry formulations of the invention that contain the three components defined hereinabove may be applied to seed masses destined for sowing or seed masses destined for consumption since the individual components of the dry powder formulation are not considered toxic to domestic livestock and/or man at the level of addition defined herein.

Formulations according to the invention are active against dried commodity storage arthropods, such as *Trigoderma* spp. (Khapra beetle), *Lasioderma serricorne* (cigarette beetle), *Ahasversus advena* (foreign grain beetle), *Sitophilus oryzae, Sitophilus granarius, Sitophilus zeamais, Rhyzopertha dominica, Ahasverus advena, Oryzaephilus* spp, such as *Oryzaephilus surinamensis, Prostephanus truncates, Rhyzopertha dominica* (lesser grain borer), *Cryptolestes* spp.

such as *Cryptolestes ferrugineus, Tribolium* spp., *Plodia interpunctella* (Indian meal moth), *Ephestia cautella* (almond moth), Mites including *Acarus siro* (flour mite), *Aceria tulipae* (gall mite) and *Psocoptera* (book lice). Typically, formulations of the invention show activity against arthropods such as *Oryzaephilus surinamensis, Sitophilus granarius* (grain weevil) and *Cryptolestes ferrugineus*.

In a further aspect of the invention there is provided use of a formulation of the invention in controlling arthropod infestation in a dry commodity storage area (facility). Dry commodity storage areas in which the use of a formulation of the invention is appropriate include dried commodity storage areas, such as grain silos and grain bins where grain is stored immediately after harvest or prior to processing. Other dried commodity storage areas include warehouses, supermarket storage facilities, ship holds, freight containers such as boxes, crates and containers associated with and/or on trains, ships, aeroplanes, and road transport vehicles. For the purposes of the present invention, the terms 'dried commodity' and 'dried commodities' are used interchangeably and encompass dried commodities including whole grains for sowing or whole grains for use as food and/or in the manufacture of processed foods, and storage sites for timber and products made from timber. Whole grains include those such as wheat, rice, barley and corn (often referred to as maize), pulses, beans, lentils and products derived from or made with dried commodities. Such dried commodity products also include processed foods such as pasta, grain flours, couscous, cereals, dried herbs, breakfast cereals, semolinas, breads, nuts (ground, flaked and/or whole nuts), snacking food, such as sweet and savoury items including biscuits, potato crisps, vegetable crisps, pretzels, cheese biscuits, dried wafers, and the like. Timber includes lumber, planking, articles made of timber such as roof scaffolding for buildings, paneling, doors and door frames, lintels, skirting board, hardboards, plywoods, furniture, and the like, and domestic livestock feed for pigs, cows, sheep and horses, and the like.

In a further aspect of the invention there is provided a method of producing a dry powder formulation of the invention comprising the steps of:
i) micronising dry electret particles;
ii) admixing dry spores of *Beauveria bassiana* such as dry spores of strain IMI 398548, with the said electret particles; and
iii) admixing dry industrial mineral earth particles with the product of step ii).

Electret particles of use in the present invention, such as carnauba wax particles are manufactured by grinding unrefined carnauba wax (available from The British Wax Refining Co. Ltd., 62 Holmethorpe Avenue, Holmethorpe Industrial Estate, Redhill, Surrey, UK), milling it, followed by a micronisation step using techniques commonly employed in the art. To obtain electret particles of a volume mean diameter of use in the invention, solid blocks of material from which electret particles can be manufactured in the form of, for example, 1 to 5 kilogram blocks or tablets may be broken down or kibbled into small millimeter-sized pieces (such as from 2-8 mm in approximate diameter in size, for example from 4 to 6 mm) in a kibbling machine. The millimeter-sized pieces are then passed through a comminuting means such as a standard mill, e.g. an Apex Comminuting mill, and milled or comminuted into particles having an approximate diameter in the range from 100 µm-500 µm, for example from 250 µm-300 µm. The micron-sized comminuted particles are then passed through a micronising apparatus, such as an AFG micronising air mill to obtain particles of a desired VMD size range as outlined herein, such as from 10 µm-40 µm, that is of use in the present invention. The skilled addressee will appreciate that such procedures for obtaining small particles are well known in the art.

The micronizing of dry electret particles may be accomplished by milling at ≤4000 rpm. If efficacy can be retained by using higher concentrations of carnauba wax (e.g. 75% wax compared to 25%) then this will reduce the breathing hazard posed by the formulation. It is also likely that increasing the carnauba wax concentration will be of benefit to product application by bulking up the product at the same spore concentration thus making it easier to apply evenly over the same surface area.

The particles of industrial mineral are preferably of a volume mean diameter of ≥25 µm or more in size, such as 10 µm-60 µm, preferably 10 µm-40 µm, for example 10 µm. Without the intention of being bound by theory, it is thought that the size of the mineral earth particles plays a role in inhibiting respiration in arthropods that come into contact with them. The industrial mineral may be selected from any industrial mineral capable of being used in the present invention, such as clays, diatomaceous earth, sand, gravel, diatomite, kaolin, bentonite, silica, barite, gypsum, montmorillonite, and talc or a mixture of two or more thereof. Preferably, the industrial mineral is selected from kaolin, talc and bentonite or a mixture of two or more thereof. Most preferably the industrial mineral is selected from kaolin and talc or a mixture thereof.

According to a further aspect of the invention, there is provided a dry powder formulation of the invention produced by the process of:
i) micronising dry electret particles;
ii) admixing dry spores of *Beauveria bassiana* such as dry spores of strain IMI 398548, with the said electret particles; and
iii) admixing dry industrial mineral earth particles with the product of step ii).

As for the method of producing a dry powder formulation of the invention containing electret particles of a volume mean diameter of use in the invention, solid blocks of material from which electret particles can be manufactured in the form of, for example, 1 to 5 kilogram blocks or tablets may be broken down or kibbled into small millimeter-sized pieces (such as from 2-8 mm in approximate diameter in size, for example from 4 to 6 mm) in a kibbling machine. The millimeter-sized pieces are then passed through a comminuting means such as a standard mill, e.g. an Apex Comminuting mill, and milled or comminuted into particles having an approximate diameter in the range from 100 µm-500 µm, for example from 250 µm-300 µm. The micron-sized comminuted particles are then passed through a micronising apparatus, such as an air classifier jet mill, for example an AFG micronising air mill to obtain particles of a desired VMD size range as outlined herein, such as from 10 µm-40 µm, that is of use in the present invention. The skilled addressee will appreciate that such procedures for obtaining small particles are well known in the art.

The micronizing of dry electret particles may be accomplished by milling at ≤4000 rpm. The spores have a much stronger influence on the VMD than the carnauba wax because they are less dense and therefore for the same weight they occupy approximately three times as much volume (visual estimate) as the carnauba wax. If efficacy can be retained by using higher concentrations of carnauba wax (e.g. 75% wax compared to 25%) then this will reduce the breathing hazard posed by the formulation. It is also likely that increasing the carnauba wax concentration will be of benefit to product application by bulking up the product at the same spore concentration thus making it easier to apply evenly over the same surface area.

The particles of industrial mineral are preferably of ≥5 μm or more in size, preferably ≥10 μm for example 10 μm. It is thought that the size of the mineral earth particles plays a role in inhibiting respiration in arthropods that come into contact with them. The industrial mineral may be selected from any industrial mineral capable of being used in the present invention, such as clays, diatomaceous earth, sand, gravel, diatomite, kaolin, bentonite, silica, barite, gypsum, montmorillonite, and talc or a mixture of two or more thereof. Preferably, the industrial mineral is selected from kaolin, talc and bentonite or a mixture of two or more thereof. Most preferably the industrial mineral is selected from kaolin and talc or a mixture thereof.

In a further aspect of the invention there is provided a method of controlling dry commodity arthropod infestation in a dry commodity storage area, wherein a dry powder formulation of the invention is presented to the surfaces of a dry commodity storage area by i) collecting the dry powder formulation in a dusting apparatus; and ii) releasing the said dry powder formulation from the said dusting apparatus and into the said dry commodity storage area.

For the purposes of the present invention "controlling dry commodity arthropod infestation" means that the arthropod population to which formulations of the invention are applied are ones that suffer losses due to death, ill health that may ultimately lead to death, and/or inability to reproduce or reduction in the ability to reproduce. Preferably, the controlling of populations of storage arthropods means that at least 80%, preferably at least 90%, of the population of arthropods dies within 28 days of application of compositions of the invention. Preferably, the populations of arthropods that are adversely affected by compositions of the invention die or at least suffer sub-lethal effects which contribute to long-term population reduction as a result of the application of dry powder formulations of the invention to the dry commodity storage area. The man skilled in the art will appreciate that the population of dry commodity storage arthropods to which the formulations of the invention are applied may be made up of one or more than one species of arthropods. Thus the method of controlling dry commodity arthropod infestation in a dry commodity storage area includes presenting a dry powder formulation of the invention to the surfaces of a dry commodity storage area.

There now follow examples and illustrating the invention. It is to be understood that the teaching of the examples is not to be construed as limiting the invention in any way.

EXPERIMENTAL SECTION

Experiment 1

Use of *Beauveria bassiana* (Bals.) for the Control of Larger Grain Borer (*Prostephanus truncatus* Horn.) of Stored Maize: Response of *Prostephanus truncatus* to Four Concentrations (CFU/Kg Maize) of *B. bassiana*, IMI 398548 in the Laboratory I. Summary An earlier study on the pathogenicity of *Beauveria bassiana*, IMI 398548 to *Prostephanus truncatus, Sitophilus zeamais* and *Teretrius nigrescens* identified *B. bassiana*, IMI 398548 to be pathogenic against adults, of *P. truncatus, S zeamais* and *T nigrescens*. To determine the most effective concentration of *B. bassiana* for the control of *P. truncatus* for the semi-field trials, a laboratory study of the response of adult *P. truncatus* to four concentrations of *B. bassiana*, IMI 398548 ($10^8$ to $10^{11}$ CFU/kg maize) was studied.

A completely randomized design (CRD) was used with 5 treatments (*P. truncatus* infested with four concentrations ($10^8$ to $10^{11}$ CFU/kg maize) of *B. bassiana*, IMI 398548 spore powder and a negative control where no *B. bassiana* was added with five replicates.

Maize grains (1250 g each) were thoroughly mixed with the various concentrations ($10^8$, $10^9$, $10^{10}$ and $10^{11}$ CFU) of *B. bassiana* IMI 398548. Each of the four treatments was then divided into five equal parts to represent 5 replications (250 g) each and placed in 500 mL Kilner jars in a completely randomized design (CRD). Adult *P. truncatus* (50) were then introduced into the treatments after 24 hours. In order to determine the viability of the fungus another 1250 g of maize was treated with $10^{11}$ colony fuming units (CFU) of *B. bassiana* and CFU were counted at the beginning and end of the trial. There was a negative control treatment in which no *B. bassiana* was added. All treatments were held at 25±2° C. and 65±5% rh.

Mortality of *P. truncatus* was assessed at 7-day intervals for 3 weeks. To determine if death were as a result of mycosis caused by *B. bassiana*, IMI 398548, insect cadavers were incubated in Petri dishes to verify colonization by the fungus.

Colonization of cadavers was observed over a period of 4 to 6 days at 26±2° C. and 65±5% rh. The results revealed that, *B. bassiana*, IMI 398548 at $10^{10}$ and $10^{11}$ CFU per kg maize resulted in significantly (P<0.05) higher mortality of adult *P. truncatus* compared to $10^8$ and $10^9$ CFU per kg maize.

For these concentrations ($10^{10}$ and $10^{11}$ CFU per kg maize), mortality of adult *P. truncatus* was 64.7-68.0% after 7 days of exposure reaching 96.0% and 98.7% respectively 14 days after treatment. In contrast, mortality of adult *P. truncatus* in $10^8$ and $10^9$ CFU per kg maize *B. bassiana*, IMI 398548 was <13% 7 days after exposure and remained less than 30%, 21 days after exposure. Mortality of *P. truncatus* in the control treatment (where no *B. bassiana* was added) was <10% at the end of 21 days.

Post-mortem mycelia and conidial growth showed that most *P. truncatus* had died from infection by the fungus with percent mycosis for the four concentrations ($10^8$, $10^9$, $10^{10}$ and $10^{11}$ CFU per kg maize) of *B. bassiana* being 97.1, 98.6, 99.6 and 99.6, respectively.

2. Objective

To evaluate the response of *Prostephanus truncatus* to four concentrations (CFU/kg maize) of *B. bassiana*, IMI 398548 in the laboratory.

3. Introduction and Study Outline

To determine the most effective concentration of *B. bassiana* for the control of *P. truncatus* for the semi-field trials, a laboratory study of the response of adult *P. truncatus* to four concentrations *B. bassiana*, IMI 398548 ($10^8$ to $10^{11}$ CFU per kg maize) was studied.

DESCRIPTION OF THE EXPERIMENT

Adults of *P. truncatus* were reared in the laboratory at Plant Protection and Regulatory Service of Ghana (PPRSD)

under ambient conditions (28±2° C., 65±5% rh). One month post adult eclosion insects were cultured on whole maize grains. Maize grains (1250 g each) were thoroughly mixed with the various concentrations ($10^8$, $10^9$, $10^{10}$ and $10^{11}$ CFU) of *B. bassiana* IMI 398548. Each of the four treatments was then divided into five equal parts to represent 5 replications (250 g) each and placed in 500 mL Kilner jars. Adult *P. truncatus* (50) were then introduced into the treatments after 24 hours. In order to determine the viability of the fungus another 1250 g of maize was treated with *B. bassiana* at $10^{11}$ CFU and colony forming units (CFU) were determined at the beginning and end of the trial. There was a negative control treatment in which no *B. bassiana* was added. All treatments were held at 25±2° C. and 65±5% rh. Mortality of *P. truncatus* was assessed at 7-day intervals for 3 weeks (days 7, 14 and 21). Post-mortem was done on cadavers of the insects to determine if death was as a result of mycosis caused by *B. bassiana*, IMI 398548.

Methods

4. Test Item Details

Materials provided by Exosect for dose response trial were:
Four sachets, each containing 3 g of formulation A ($10^8$ CFU per kg maize).
Four sachets, each containing 3 g of formulation B ($10^9$ CFU per kg maize).
Four sachets, each containing 3.2 g of formulation C ($10^{10}$ CFU per kg maize).
Four sachets, each containing 4.5 g of formulation D ($10^{11}$ CFU per kg maize).
A: 2 g kaolin+0.3 g Entostat®+0.001 g spores/Kg maize
B: 2 g kaolin+0.3 g Entostat®+0.01 g spores/Kg maize
C: 2 g kaolin+0.3 g Entostat®+0. g spores/Kg maize
D: 2 g kaolin+0.3 g Entostat®+1.0 g spores/Kg maize
Source of Insects The one month post adult eclosion of *P. truncatus* used for the trial, were reared on whole maize grains at 28±2° C. and 65±5% rh in the Entomology laboratory of the Biocontrol Unit, Plant Protection and Regulatory Service of MOFA, Accra.

Determination of Concentrations of *Beauveria bassiana*, IMI 398548 for the Protection of Stored Maize Against *Prostephanus truncatus*

To determine the most effective concentration of *B. bassiana*, IMI 398548 formulation for stored maize protection against *P. truncatus*, a laboratory study was undertaken with four concentrations ($10^8$, $10^9$, $10^{10}$ and $10^{11}$ CFU per kg maize) of *B. bassiana*, IMI 398548.

Maize ('Obatanpa' cultivar) was stored in a freezer, at −4° C. for 2 days. The maize was then removed, oven dried for a day at 50° C. and left for a further day to cool. Maize (2500 g) was treated with 4.5 g of *B. bassiana* ($1 \times 10^{11}$ CFU/kg maize) and divided into 10 jars containing aliquots of 250 g each. Five of these jars were used for mortality assessment whilst, the other five were used for initial and final viability tests. For the other concentrations, a 1,250 g of maize each was mixed thoroughly with 3.2 g of *B. bassiana* at $10^{10}$ CFU/kg maize, 3 g of *B. bassiana*, at $10^8$ and $10^9$ CFU and divided into five equal parts (250 g) representing five replications. There was a negative control in which no *B. bassiana* was added. The grains were left for 24 hours after which 50 unsexed *P. truncatus* were introduced into each jar. The treatments were left at laboratory conditions of 25±2° C. and 65±5% rh. The temperature and relative humidity in the Entomology laboratory of the Department of Crop Science, Legon where this bioassay was carried out was monitored using a data logger.

After the insects were introduced, 5 g of maize grains was sampled from each replicate of *B. bassiana* at $1 \times 10^{11}$ CFU/kg maize (which had no insects) and washed in 10 mL sterile 0.05% Tween 80. The suspension was agitated slightly by shaking gently for some few minutes before performing a 10-fold serial dilution resulting in 8 dilutions. A 200 µl aliquots of each dilution was inoculated in duplicate on Sabouraud Dextrose Agar (SDA) using the spread plate technique and incubated for 4 days to determine the number of colony forming units (CFU) per mL Mortality of *P. truncatus* was recorded at 7-day intervals for three weeks by empting each jar on laboratory trays. Dead insects were removed at each assessment time and surface sterilized in 2% sodium hypochlorite for 1 minute, followed by two rinses in sterile distilled water for 1 minute. The cadavers from each treatment were then transferred onto Whatman filter papers moistened with 1 mL sterile distilled water, placed on 9 cm Petri dishes and sealed with Parafilm. Insects on moistened filter papers were kept apart and incubated at ambient conditions and examined after 6 days for growth of *B. bassiana*, IMI 398548.

On day 21, fungal viability was determined as done on the first day of the experiment by determining CFU count per mL. Grains were sieved to separate grain powder from the kernel. The weight of the powder, kernel and number of live *P. truncatus* in each jar were recorded. Percentage weight loss (L) was calculated using the formula below $$L=[(Wi-Wf)/Wi)] \times 100,$$

where, Wi is the initial weight of grains, and Wf is the final weight of grains.

The cumulative percentage mortality data and percent mycosis were arcsine transformed; Additional data collected were the total number live *P. truncatus* at day 21, weight of kernel and powder at the end of the experiment, number of colonies formed by the highest concentration at the start and end of the trial.

Data were subjected to analysis of variance (ANOVA). Least significant difference ($LSD_5\%$) was used to separate means. The statistical analysis was accomplished using Genstat statistical software ($9^{th}$) edition.

5. Test System

All insects totaling 1000 of unsexed adult *P. truncatus* were supplied by Plant Protection and Regulatory Service Ghana (PPRSD). The insects were reared on whole maize grains at the Biocontrol Unit of PPRSD under ambient conditions (28±2° C. and 65±5% rh). Insects used were approximately one month post adult eclosion.

6. Test Location

The dose response bioassay was conducted in the Entomology laboratory of the Department of Crop Science, Legon at an average room temperature of 25±2° C. and 65±5% rh. Insect cadavers were incubated at 26±2° C. and 65±5% rh respectively in the Pathology laboratory of the Department of Crop Science, University of Ghana.

7 Experimental Design

A completely randomized design (CRD) was used with 5 treatments (*P. truncatus* infested with four concentrations ($10^8$ to $10^{11}$ CFU/kg maize) of *B. bassiana*, IMI 398548 spore powder and a negative control which had no *B. bassiana* added with five replicates. Each replicate contained 50 adult *P. truncatus*.

8. Application Details and Regime

The weight of maize kernel and powder at the end of the experiment were weighed using an electronic balance.

9. Statistical Analysis

Control mortality at the end of the trial (21 days) was relatively low (<10%), consequently, cumulative percentage mortality data were not corrected for the corresponding control mortality (Abbott, 1925).

The cumulative percentage mortality and percent mycosis data were arcsine transformed; Additional data collected were the total number of live *P. truncatus* at day 21, weight of kernel and powder at the end of the experiment, number of colonies formed from *B. bassiana* at $10^{11}$ CFU/kg maize (which had no insects) at the start and end of the trial (Appendix 3-10).

Data were subjected to analysis of variance (ANOVA). Least significant difference ($LSD_5$%) was used to separate means. The statistical analysis was accomplished using Genstat statistical software ($9^{th}$) edition.

10. Protocol Deviations

The proposed protocol was strictly adhered to except that, there was no mention of 'control' which we deemed fit and therefore included in this trial.

11. Results

Response of *Prostephanus truncatus* to four concentrations (CFU/kg maize) of *B. bassiana*, IMI 398548 in the laboratory.

The response of *P. truncatus* to *B. bassiana*, IMI 398548 was evaluated by applying four concentrations of *B. bassiana* ($10^8$, $10^9$, $10^{10}$ and $10^{11}$ CFU) per kg maize for 21 days to determine their effect on the mortality of *P. truncatus*. Quantification of the mortality of the one month post adult eclosion *P. truncatus* was made at 7, 14 and 21 days after infestation. For all concentrations, the mortality of *P. truncatus* increased with increasing days of exposure. *Beauveria bassiana*, IMI 398548 at $10^{10}$ and $10^{11}$ CFU per kg maize resulted in significantly (P<0.05) higher mortality of adult *P. truncatus* compared to $10^8$ and $10^9$ CFU per kg maize. For these concentrations ($10^{10}$ and $10^{11}$), mortality of *P. truncatus* was 64.7-68.0% after 7 days of exposure reaching 96.0% and 98.7% respectively after 14 days. In contrast, mortality of adult *P. truncatus* in *B. bassiana*, IMI 398548 at $10^8$ and $10^9$ CFU per kg maize was <13% after 7 days of exposure and remained less than 30%, 21 days after exposure. Mortality of *P. truncatus* in the control treatment (where no *B. bassiana* was added) was <10% at the end of 21 days (Table 1).

TABLE 1

Cumulative percentage mortality (%) of *P. truncatus* infested with spore powder of *B. bassiana* (CFU per kg maize) and incubated for 7, 14 and 21 days at 25 ± 2° C. and 65 ± 5% rh in the laboratory.

| Dose of *B. bassiana* | Cumulative mortality (%) at days after treatment | | |
|---|---|---|---|
| (CFU/per kg maize) | 7 | 14 | 21 |
| $1 \times 10^8$ | 5.33 | 10.00 | 14.67 |
| $1 \times 10^9$ | 12.67 | 22.00 | 28.00 |
| $1 \times 10^{10}$ | 64.67 | 96.00 | 100.00 |
| $1 \times 10^{11}$ | 68.00 | 98.67 | 100.00 |
| Control | 1.33 | 4.67 | 9.33 |
| LSD (p < 0.05) | 6.97 | 4.20 | 3.87 |

Mean Percentage Weight Loss of Kernel after Infestation by *P. truncatus* Treated with *B. bassiana* ($10^8$ to $10^{11}$ CFU) Per Kg Maize and Incubated at 25±2° C. and 65±5% Rh for 21 Days.

The percentage weight loss of maize kernel caused by *P. truncatus* treated with *B. bassiana* at $10^8$ and $10^9$ CFU per kg maize were not significantly different from the control treatment. The weight loss (%) of kernel produced by *P. truncatus* on *B. bassiana* at $10^{10}$ and $10^{11}$ CFU per kg maize were similar but differed significantly (P<0.05) from the control. A significantly (P<0.05) higher grain weight loss was recorded on maize grains treated with *B. bassiana*, IMI 398548 at $10^8$ and $10^9$ CFU per kg maize compared with $10^{10}$ and $10^{11}$ CFU per kg maize after infestation by *P. truncatus* for 21 days (Table 2).

TABLE 2

Mean (%) weight loss of kernel after infestation by *P. truncatus* infested with *B. bassiana* ($10^8$ to $10^{11}$ CFU) per kg maize and incubated for 21 days at 25 ± 2° C. and 65 ± 5% rh in the laboratory.

| Dosage (CFU/kg maize) | % weight loss of kernel |
|---|---|
| $1 \times 10^8$ | 1.554 |
| $1 \times 10^9$ | 1.460 |
| $1 \times 10^{10}$ | 0.439 |
| $1 \times 10^{11}$ | 0.400 |
| Control | 1.528 |
| LSD (p < 0.05) | 0.2927 |

Viability and persistence of *B. bassiana*, IMI 398548 at $10^{11}$ CFU per kg maize The number of colonies formed by the highest concentration ($10^{11}$ CFU per kg maize) at day 1 was not significantly different from those at day 21 (t=0.10, t-prob.=0.922, df=4). Post-mortem mycelia and conidial growth showed that most insects had died from infection by the fungus with percent mycosis for the four concentrations ($10^8$, $10^9$, $10^{10}$ and $10^{11}$ CFU per kg maize) of *B. bassiana* being 97.1, 98.6, 99.6 and 99.6 respectively (Table 3).

TABLE 3

Mean (%) mycosis of *P. truncatus*, infested with *B. bassiana* ($10^8$ to $10^{11}$ CFU) per kg maize and incubated for 4 days at 26 ± 2° C. and 65 ± 5% rh in the laboratory.

| Dosages (CFU/kg maize) | Percentage mycosis |
|---|---|
| $1 \times 10^8$ | 97.1 |
| $1 \times 10^9$ | 98.6 |

TABLE 3-continued

Mean (%) mycosis of *P. truncatus*, infested with *B. bassiana* ($10^8$ to $10^{11}$ CFU) per kg maize and incubated for 4 days at 26 ± 2° C. and 65 ± 5% rh in the laboratory.

| Dosages (CFU/kg maize) | Percentage mycosis |
| --- | --- |
| 1 × $10^{10}$ | 99.6 |
| 1 × $10^{11}$ | 99.6 |
| LSD (p < 0.05) | 4.9 |

Analysis of variance was made on arcsine percentage sporulated data

12. Discussion

This is the first report of a new isolate (IMI 398548) of *B. bassiana* for the control of *P. truncatus*. *B. bassiana*, IMI 398548 at $10^{10}$ and $10^{11}$ CFU per kg maize resulted in higher mortality of adult *P. truncatus* compared to $10^8$ CFU and $10^9$ per kg maize. In the present study the highest mortality (64.7-68.0%) of *P. truncatus* was achieved in *B. bassiana* at $10^{10}$ and $10^{11}$ CFU per kg maize respectively at 25±2° C. and 65±5% rh after 7 days of exposure reaching 96.0% and 98.7% respectively 14 days after treatment.

In the current study, viability of conidia of *B. bassiana* at $10^{11}$ CFU per kg maize persisted though out the study period for 21 days. This demonstrates the requirement that, mycopesticide formulation should persist in the environment for a considerable time after application (Burges, 1998). A similar result is envisaged under semi field conditions since conditions under grain storage in Ghana are more stable and similar to the conditions observed in the study.

One of the enormous advantages of using microbial control systems is that disease infection cycling occurs when infected and dead insects increase the amount of inocula after sporulation to effectively increase the persistence of the mycopesticide (Hidalgo et al., 1998). During this study insect cadavers were consistently removed from maize grains, however, *B. bassiana* mycelia and spore sporulation appeared 3-4 days after incubation and completely covered the cadavers of *P. truncatus*, indicating the existence of an adequate dose transfer from treated maize grains. The present study indicated the possibility of successfully controlling *P. truncatus* on stored and infested maize using spore powder of *B. bassiana* at 1×$10^{10}$ CFU per kg maize in the laboratory.

13. References

Abbott, W. S. (1925). A method of computing the effectiveness of an insecticide. *Journal of Economic Entomology*. 18: 265-267.

Burges H. D. (1998). Formulation of mycoinsecticides, In H. D. Burges, (ed.), Formulation of microbial biopesticides: beneficial microorganisms, nematodes and seed treatments: Kluwer Academic Publisher, Dordrecht pp 132-185.

Hidalgo, E., D. Moore & G. Le Patourel. (1998). The effect of different formulations of *Beauveria bassiana* on *Sitophilus zeamais* in stored maize. *Journal of Stored Product Research* 34: 171-179.

Experiment 2

Pilot Scale Trial of Biopesticide Formulations in the Grain Store

1. Aim

To assess dry conidia of an isolate of the entomopathogenic fungus *Beauveria bassiana* at different concentrations against three species of insect when applied to arenas made of galvanized steel and stored in the grain store environment.

2. Introduction

The aim of this study was to conduct a range finding test to determine the effective dose of dry conidia powder of *B. bassiana* IMI398548 (a biologically pure culture of a novel isolate of *Beauveria bassiana* deposited with CABI, Bakeham Lane, Egham, Surrey, TW20 9TY, UK on 11 May 2010 in accordance with the Budapest Treaty for the deposit of microorganisms and accorded the deposit number of IMI 398548) against three beetle species when applied to steel arenas in the Fera grain store. Entostat® was not included in this study as the aim was to evaluate the effect of the conidia in the absence of any material that may enhance the effect.

3. Materials 3.1 Fungal Isolate.

The *B. bassiana* isolate (IMI398548) was produced by Somycel S. A. using a mass production method and was checked using in-house quality control (QC) procedures. The final product contained 9.3×$10^{10}$ conidia/g. The isolate was designated as TA 2645 for the purposes of this study and was stored in a refrigerator at 4-8° C.

3.2 K-Obiol

K-Obiol EC25 (TA 2644) (containing 25 g/l active ingredient) was obtained from Killgerm Chemicals and was used as the positive control. Prior to treatment the pesticide was stored in a secure cabinet situated in a laboratory with a mean temperature of 20° C.±0.5 and ambient relative humidity (r.h.). A solution containing the recommended field application rate was made up in water, according to the manufacturer's recommendations, on the day of use.

3.3 Insects

Three species of insect were tested. These were *Oryzaephilus surinamensis* strain Tram (saw-toothed grain beetle), *Sitophilus granarius* strain Gainsborough (grain weevil) and *Cryptolestes ferrugineus* strain Stow (rust-red grain beetle). Insects used were of mixed age and sex. All three species were used simultaneously within the arena. Insects were provided by the Invertebrate Supply Unit at Fera and reared according to Fera Standard Operating Procedures (ISU/018 and ISU/034 revision 3).

3.4 Construction of Arenas

The arenas were constructed within Fera's grain storage facility. Insects were confined to squares of galvanized steel (500×500×0.8 mm) within circular galvanized steel rings (approx 450 mm diameter, 150 mm high). The inside surface of the steel ring was coated with Fluon (Whitford Plastics, UK) to prevent escape of the insects. The rings were sealed to the steel sheet using decorators caulk so that insects could not get under the ring. A refuge made from a piece of electrical conduit (25×16×100 mm), containing kibbled wheat to provide food for the insects, was placed in the centre of each ring approximately 1 hour after introduction of the insects.

4. Methods 4.1 Treatment of Arenas

The treatments were as follows:
No treatment (negative control)
Water (control for K-Obiol)
K-Obiol (positive control) applied at 0.05 liters/m$^2$
1×$10^9$ conidia/m$^2$ $1 \times 10^{10}$ conidia/m$^2$
$1 \times 10^{11}$ conidia/m$^2$ Treatments were assigned to each arena using a randomized block design. There were five replicate rings for each treatment.

The conidia were weighed out on to small pieces of aluminium foil, which was folded to prevent loss of material during transportation to the grain store. The appropriate amount of material was evenly distributed across the floor area of the assigned rings using a small brush.

The K-Obiol and water controls were treated by spraying the solution to achieve a coverage of 0.05 liters/$m^2$. A known volume (12.5 ml) of pesticide solution or water was applied to the steel squares using a hand held 'De Vilbis' laboratory sprayer (EBGF-047).

The spray gun was held approximately 20 cm above the surface of the square and the pesticide or water was sprayed onto the surface, working progressively across and down the square in zigzag movements, in order to obtain an even treatment across the surface.

4.2 Addition of Insects

Insects were counted in the laboratory, transported in vials and released into the steel rings 24 hours after treatment. All three species were present within each of the steel rings and 50 insects of each species were used in each replicate. The refuge containing kibbled wheat was added to the arena approximately one hour after the introduction of the insects.

4.3 Assessment of Insects

Insect mortality was assessed after 14 and 28 days. Insects were collected from the rings into labelled glass tubes with the aid of an artist's paintbrush. Refuges were removed from the rings and placed in labelled self-seal plastic bags. The numbers of live and dead insects of each species within each steel ring and the refuge was recorded. Live insects were returned to the rings from which they were removed after the 14-day assessment for re-assessment of mortality after 28 days. The refuges were also returned to the rings from which they had been removed.

4.4 Monitoring of Environmental Conditions

Temperature was monitored throughout the trial using calibrated thermocouples (Type-T with a beaded tip and PTFE insulation (−50 to +250° C.)) linked to a 'Squirrel' (model no. 1045) temperature logger (EBGF 121/122). Temperatures were logged every 60 minutes. The data was downloaded and analysed using 'SquirrelView' software. Temperature and humidity were also monitored using Tinytag dataloggers (TGP 1500, Gemini Dataloggers Ltd, UK) (OPA0/AppEnt 001-003) positioned in three of the arenas. Lights within the store were switched on during treatment and assessments, but remained off at all other times.

4.5 Statistical Analysis

The difference in mortality between treatments was analysed by a generalized linear model (GLM) with a logit link function. Post-hoc tests were used to test for differences between the treatments by comparison of the least significant difference for the treatments.

5. Results 5.1 Environmental Conditions

The average temperature recorded in the grain store throughout the trial was 14.3° C. with a minimum of 7.2° C. and a maximum of 20.9° C. There was very little variation in temperature observed between the arenas. The average humidity during the trial recorded using the Tinytag dataloggers was 81.7% with a minimum of 51.2% and a maximum of 98.2%.

5.2 Insect Mortality Data

Application of K-Obiol at the recommended rate resulted in 100% mortality of all three beetle species tested after 14 days exposure. Although an accurate assessment was not made, observation of the arenas after 24 hours indicated that many, if not all, of the beetles in the arenas treated with K-Obiol were dead. As the aim of this experiment was to determine the effective application rate of the *B. bassiana* isolate, the K-Obiol treatment and the water control were not included in the statistical analysis.

There was a highly significant effect of treatment with the different doses of conidia on the mortality for all three beetle species after 14 days exposure (GLM $F_{3.19}$=79.76, P<0.001, $F_{3.19}$=31.34, P<0.001 and $F_{3.19}$=106.64, P<0.001 for *S. granarius, O. surinamensis* and *C. ferrugineus* respectively (Table 1). There was no significant difference in mortality compared with the control at the lowest application rate tested ($1\times10^9$ conidia/$m^2$) for *S. granarius* and *O. surinamensis* (P>0.05). There was a significant difference in mortality compared with the control at the highest application rate tested ($1\times10^{11}$ conidia/$m^2$) for all three beetle species.

The intermediate application rate ($1\times10^{10}$ conidia/$m^2$) resulted in significant mortality of *S. granarius* and *C. ferrugineus* after 14 days exposure. Application of $1\times10^{11}$ conidia/$m^2$ resulted in the highest levels of mortality for all three beetle species, and this mortality was significantly greater than that with $1\times10^{10}$ conidia/$m^2$.

TABLE 1

Derived mean % mortality of insects 14 days after exposure to different treatments. % mortality is expressed in terms of the number of insects recovered for each species. Figures in parentheses are the derived 95% confidence intervals.

| | *S. granarius* | *O. surinamensis* | *C. ferrugineus* |
|---|---|---|---|
| Control | 1.2a | 2.6a | 5.2a |
| | (0.2, 7.8) | (0.4, 17.0) | (2.3, 11.7) |
| $1\times10^9$ conidia/$m^2$ | 4.7a | 3.6a | 22.1b |
| | (1.8, 11.8) | (0.7, 16.4) | (15.2, 31.1) |
| $1\times10^{10}$ conidia/$m^2$ | 31.6b | 13.6a | 68.1c |
| | (22.7, 42.1) | (5.9, 28.0) | (58.5, 76.4) |
| $1\times10^{11}$ conidia/$m^2$ | 86.0c | 77.5b | 98.8d |
| | (77.0, 91.9) | (62.2, 87.8) | (93.2, 99.8) |

In each column means followed by the same letter are not significantly different (GLM; P > 0.05).

There was a highly significant effect of treatment with the different doses of conidia on the mortality for all three beetle species after 28 days exposure (GLM $F_{3.19}$=171.61, P<0.001, $F_{3.19}$=87.14, P<0.001 and $F_{3.19}$=54.89, P<0.001 for *S. granarius, O. surinamensis* and *C. ferrugineus* respectively (Table 2). All three application rates of conidia resulted in significant levels of mortality for *S. granarius* and *O. surinamensis* compared with the control (P<0.05). The intermediate and highest application rates resulted in significant mortality of *O. surinamensis* compared with the control (P<0.05). Application of $1\times10^{11}$ conidia/$m^2$ resulted in the highest levels of mortality for all three beetle species, and this mortality was significantly greater than that with $1\times10^{10}$ conidia/$m^2$.

TABLE 2

Derived mean % mortality of insects 28 days after exposure to different treatments. % mortality is expressed in terms of the cumulative number of dead insects recovered after 14 and 28 days divided by the total of the number of insects recovered after 28 days and the number of dead insects after 14 days. Figures in parentheses are the derived 95% confidence intervals.

|  | S. granarius | O. surinamensis | C. ferrugineus |
|---|---|---|---|
| Control | 1.6a | 14.7a | 25.5a |
|  | (0.4, 5.6) | (9.0, 23.2) | (16.4, 37.5) |
| $1 \times 10^9$ conidia/m$^2$ | 13.1b | 10.8a | 45.4b |
|  | (8.6, 19.6) | (6.2, 18.1) | (34.1, 57.2) |
| $1 \times 10^{10}$ conidia/m$^2$ | 63.1c | 38.7b | 92.8c |
|  | (54.9, 70.6) | (29.9, 48.2) | (83.9, 96.9) |
| $1 \times 10^{11}$ conidia/m$^2$ | 97.6d | 96.1c | 99.6c |
|  | (93.4, 99.1) | (89.9, 98.5) | (86.3, 99.9) |

In each column means followed by the same letter are not significantly different (GLM; $P > 0.05$).

6. Discussion

The trial was designed to determine the effective application rate of a dry conidia powder of *B. bassiana* IMI398548 for three beetle species when applied as a surface treatment in a grain store under typical UK conditions. A dose response was observed for all three beetle species and this was particularly evident after 28 days exposure to the treated surface. The highest application rate used ($1 \times 10^{11}$ conidia/m$^2$) resulted in significant mortality of all three beetle species after 14 and 28 days compared with the control. The lowest application rate $1 \times 10^9$ conidia/m$^2$ did not result in significant mortality of *S. granarius* or *O. surinamensis* after 14 days exposure and no significant mortality of *O. surinamensis* after 28 days exposure. Of the three beetle species tested, *C. ferrugineus* was the most susceptible to treatment with isolate IMI398548.

In Conclusion:

An application rate greater than $1 \times 10^9$ conidia/m$^2$ of IMI398548 is needed for effective control of the three beetle species tested.

An application rate of $1 \times 10^{11}$ conidia/m$^2$ resulted in mortalities greater than 96% for all three beetle species after 28 days exposure.

Experiment 3

Pilot Scale Trial of Bio-Pesticide Formulations in the Grain Store—Formulation with Kaolin

1. Aim

To assess the formulation of an isolate of the entomopathogenic fungus *Beauveria bassiana* mixed with kaolin at different concentrations against two species of insect when applied to arenas made of galvanized steel and stored in the grain store environment.

2. Introduction

The aim of this study was to determine the effectiveness of a powder formulation of *B. bassiana* IMI398548 mixed with kaolin and Entostat® against two beetle species when applied to steel arenas in the Fera grain store.

3. Materials

3.1 Fungal Isolate

The *B. bassiana* isolate (IMI398548) was produced by Somycel S. A. using a mass production method and was checked using in-house quality control (QC) procedures. The final product contained $3.8 \times 10^{10}$ conidia/g. The isolate was designated as TA 2654 for the purposes of this study and was stored in a refrigerator at 4-8° C.

3.2 Kaolin and Entostat®

The kaolin used was produced by Opal Omega and was supplied to Fera by Exosect Ltd. The Entostat® was supplied by Exosect Ltd. Both the kaolin and Entostat® were kept at room temperature.

3.3 Insects

Two species of insect were tested. These were *Oryzaephilus surinamensis* strain Tram (saw-toothed grain beetle), and *Cryptolestes ferrugineus* strain Stow (rust-red grain beetle). Insects used were of mixed age and sex. Both species were used simultaneously within the arena. Insects were provided by the Invertebrate Supply Unit at Fera and reared according to Fera Standard Operating Procedures (ISU/018 revision 4 and ISU/034 revision 3).

3.4 Construction of Arenas

Insects were confined to squares of galvanized steel (500×500×0.8 mm) within circular galvanized steel rings (approx 450 mm diameter, 150 mm high). The inside surface of the steel ring was coated with Fluon (Whitford Plastics, UK) to prevent escape of the insects. The rings were sealed to the steel sheet using decorators caulk so that insects could not get under the ring. A refuge made from a piece of electrical conduit (25×16×100 mm), containing kibbled wheat to provide food for the insects, was placed in the centre of each ring approximately 1 hour after introduction of the insects.

4. Methods

4.1 Treatment of Arenas

The treatments were as follows:
1. No treatment (control)
2. Entostat®+kaolin (weight to equal that used in the IMI398548 $5 \times 10^9$ conidia/m$^2$+Entostat®+kaolin (1:3:20) formulation)=Carrier low
3. Entostat®+kaolin (weight to equal that used in the IMI398548 $1 \times 10^{10}$ conidia/m$^2$+Entostat®+kaolin (1:3:20) formulation)=Carrier high
4. IMI398548 $5 \times 10^9$ conidia/m$^2$
5. IMI398548 $1 \times 10^{10}$ conidia/m$^2$
6. IMI398548 $5 \times 10^9$ conidia/m$^2$+Entostat®+kaolin (1:3:20)
7. IMI398548 $5 \times 10^9$ conidia/m$^2$+Entostat®+kaolin (1:6:40)
8. IMI398548 $1 \times 10^{10}$ conidia/m$^2$+Entostat®+kaolin (1:3:20)

Treatments were assigned to each arena using a randomized block design. There were five replicate rings for each treatment.

The formulations were made up by weighing out the individual components into a glass vial and mixing using a vortex mixer. The conidia and formulations required to treat the arenas were weighed out on to small pieces of aluminium foil, which were then carefully folded to protect the contents during transfer to the grain store. The appropriate amount of material was evenly distributed across the floor area of the assigned rings using a small brush. The calculated amount of material added to the arenas for each treatment is shown in Table 1.

TABLE 1

Calculated amount of material added to the arenas for each treatment.

| Treatment | Conidia (g) | Entostat (g) | Kaolin (g) | Total (g) |
|---|---|---|---|---|
| Control | 0 | 0 | 0 | 0 |
| Carrier low | 0 | 0.0627 | 0.418 | 0.4807 |
| Carrier high | 0 | 0.1254 | 0.836 | 0.9614 |
| $5 \times 10^9$ conidia/m$^2$ | 0.0209 | 0 | 0 | 0.0209 |
| $1 \times 10^{10}$ conidia/m$^2$ | 0.0418 | 0 | 0 | 0.0418 |
| $5 \times 10^9$ conidia/m$^2$ 1:3:20 | 0.0209 | 0.0627 | 0.418 | 0.5016 |
| $5 \times 10^9$ conidia/m$^2$ 1:6:40 | 0.0209 | 0.1254 | 0.836 | 0.9823 |
| $1 \times 10^{10}$ conidia/m$^2$ 1:3:20 | 0.0418 | 0.1254 | 0.836 | 1.0032 |

4.2 Addition of Insects

Insects were counted in the laboratory, transported in vials and released into the steel rings 24 hours after treatment. Both species were present within each of the steel rings and 50 insects of each species were used in each replicate. The refuge containing kibbled wheat was added to the arena approximately one hour after the introduction of the insects.

4.3 Assessment of Insects

Insect mortality was assessed after 7 days. Insects were collected from the rings into labelled glass tubes with the aid of a battery operated suction device. Refuges were removed from the rings and placed in labelled self-seal plastic bags. The numbers of live and dead insects of each species within each steel ring and the refuge was recorded.

4.4 Monitoring of Environmental Conditions

Temperature and humidity were monitored using Tinytag dataloggers (TGP 1500, Gemini Dataloggers Ltd, UK) (OPA0/AppEnt 002 and 003) located in two positions around the arenas. Lights within the store were switched on during treatment and assessments, but remained off at all other times.

4.5 Statistical Analysis

The difference in mortality between treatments was analysed by a generalized linear model (GLM) with a logit link function. Post-hoc tests were used to test for differences between the treatments by comparison of the least significant difference for the treatments. When treatment mortalities were 0% or 100% a least significant difference value could not be obtained and post-hoc comparisons based on the least significant difference were therefore not possible for these treatments.

5. Results 5.1 Environmental Conditions

The average temperature recorded in the grain store throughout the trial was 15.8° C. with a minimum of 13.1° C. and a maximum of 19.5° C. The average humidity during the trial recorded using the Tinytag dataloggers was 81.9% with a minimum of 61.9% and a maximum of 98.8%.

5.2 Insect Mortality Data

There was a highly significant effect of treatment on the mortality of *O. surinamensis* and *C. ferrugineus* after 7 days exposure (GLM $F_{7,36}$=11.11, P<0.001 and $F_{7,36}$=7.98, P<0.001 respectively). See Table 2, below.

Mortality in the treatments with the conidia alone at application rates of 5×109 or 1×1010 conidia/m$^2$ was not significantly different to the mortality in untreated (control) arenas for either *O. surinamensis* or *C. ferrugineus* (Table 2). The carrier used alone at the same application rate as in the 5×10$^9$ conidia/m$^2$ 6:40 and 1×10$^{10}$ conidia/m$^2$ 3:20 (Carrier high) resulted in significant mortality of *O. surinamensis* and *C. ferrugineus* (P<0.05) compared with the control (Table 2). The carrier used alone at the same application rate as in the 5×10$^9$/m$^2$ 3:20 (Carrier low) resulted in significant mortality of *O. surinamensis* compared with the control treatments. The highest mortalities for both *O. surinamensis* and *C. ferrugineus* were seen in the treatments with IMI398548, Entostat® and kaolin (Table 2).

TABLE 2

Derived mean % mortality of insects 7 days after exposure to different treatments. % mortality is expressed in terms of the number of insects recovered for each species. Figures in parentheses are the derived 95% confidence intervals.

| | O. surinamensis | C. ferrugineus |
|---|---|---|
| Control | 22.6a | 13.83a |
| | (8.2, 48.7) | (3.0, 45.5) |
| Carrier low | 58.6b | 49.3a, b |
| | (36.7, 77.7) | (25.3, 73.6) |
| Carrier high | 79.4b, c | 86.2b, c |
| | (55.3, 92.3) | (54.7, 97.0) |
| $5 \times 10^9$/m$^2$ | 19.7a | 20.4a |
| | (7.7, 42.0) | (6.5, 48.5) |
| $1 \times 10^{10}$/m$^2$ | 17.2a | 28.4a |
| | (6.0, 40.5) | (11.1, 55.7) |
| $5 \times 10^9$/m$^2$ 6:40 | 91.3b, c | 87.6b, c |
| | (56.9, 98.8) | (52.2, 97.8) |
| $5 \times 10^9$/m$^2$ 3:20 | 93.4c | 90.8c |
| | (68.3, 98.9) | (62.3, 98.3) |
| $1 \times 10^{10}$/m$^2$ 3:20 | 100 | 100 |

In each column means followed by the same letter are not significantly different (GLM; P > 0.05).

6. Conclusions

High levels of mortality (87-100%) were observed for *O. surinamensis* and *C. ferrugineus* in treatments with *B. bassiana* IMI398548, Entostat® and kaolin after 7 days exposure in treated arenas.

The Entostat® and kaolin carrier alone resulted in statistically significant levels of mortality for *O. surinamensis* at both application rates compared with the control and conidia only treatments. The greater amount of the carrier gave the higher level of mortality.

The Entostat® and kaolin carrier alone at the higher application rate resulted in a significant increase in mortality of *C. ferrugineus* compared with the control and conidia only treatments. The lower application rate of Entostat® and kaolin caused nearly 50% mortality of *C. ferrugineus*, but this was not significantly different from the mortality in control treatments (13.8%).

List of Standard Operating Procedures

ISU 018 revision 3 General culturing procedure for stored product beetles

ISU 034 revision 3 Food preparation and general culture requirements within the ISU Experiment 4

Pilot Scale Trial of Biopesticide Formulations in the Grain Store—Formulation with Talc 1. Aim To assess the formulation of an isolate of the entomopathogenic fungus *Beauveria bassiana* mixed with talc at different concentrations against two species of insect when applied to arenas made of galvanized steel and stored in the grain store environment.

2. Introduction

The aim of this study was to determine the effectiveness of a powder formulation of *B. bassiana* I Ml 398548 mixed with talc and Entostat® against two beetle species when applied to steel arenas in the Fera grain store.

3. Materials

3.1 Fungal Isolate

The *B. bassiana* isolate (IMI398548) was produced by Somycel S. A. using a mass production method and was checked using in-house quality control (QC) procedures. The final product contained $3.8 \times 10^{10}$ conidia/g. The isolate was designated as TA 2654 and was stored in a refrigerator at 4-8° C.

3.2 Magnesium Silicate (Talc) and Entostat®

The magnesium silicate (talc) used was supplied by Alfa Aesar, UK. The Entostat® was supplied by Exosect Ltd. Both the talc and Entostat® were kept at room temperature (approximately 20° C.).

3.3 Insects

Two species of insect were tested. These were *Oryzaephilus surinamensis* strain Tram (saw-toothed grain beetle), and *Cryptolestes ferrugineus* strain Stow (rust-red grain beetle). Insects used were of mixed age and sex. Both species were used simultaneously within the arena. Insects were provided by the Invertebrate Supply Unit at Fera and reared according to Fera Standard Operating Procedures (ISU/018 revision 4 and ISU/034 revision 3).

3.4 Construction of Arenas

Insects were confined to squares of galvanized steel (500×500×0.8 mm) within circular galvanized steel rings (approx. 450 mm diameter, 150 mm high). The inside surface of the steel ring was coated with Fluon (Whitford Plastics, UK) to prevent escape of the insects. The rings were sealed to the steel sheet using decorators caulk so that insects could not get under the ring. A refuge made from a piece of electrical conduit (25×16×100 mm), containing kibbled wheat to provide food for the insects, was placed in the centre of each ring approximately 1 hour after introduction of the insects.

4. Methods

4.1 Treatment of Arenas

The treatments were as follows:
1. No treatment (control)
2. Entostat®+talc (weight to equal that used in the IMI398548 $5 \times 10^9$ conidia/m²+Entostat®+talc (1:3:20) formulation)=Carrier low
3. Entostat®+kaolin (weight to equal that used in the IMI398548 $1 \times 10^{10}$ conidia/m²+Entostat®+talc (1:3:20) formulation)=Carrier high
4. IMI398548 $5 \times 10^9$ conidia/m²
5. IMI398548 $1 \times 10^{10}$ conidia/m²
6. IMI398548 $5 \times 10^9$ conidia/m²+Entostat®+talc (1:3:20)
7. IMI398548 $5 \times 10^9$ conidia/m²+Entostat®+talc (1:6:40)
8. IMI398548 $1 \times 10^{10}$ conidia/m²+Entostat®+talc (1:3:20)

Treatments were assigned to each arena using a randomized block design. There were five replicate rings for each treatment.

The formulations were made up by weighing out the individual components into a glass vial and mixing using a vortex mixer. The conidia and formulations required to treat the arenas were weighed out on to small pieces of aluminium foil, which were then carefully folded to protect the contents during transfer to the grain store. The appropriate amount of material was evenly distributed across the floor area of the assigned rings using a small brush. The calculated amount of material added to the arenas for each treatment is shown in Table 1.

TABLE 1

Calculated amount of material added to the arenas for each treatment.

| Treatment | Conidia (g) | Entostat (g) | Talc (g) | Total (g) |
|---|---|---|---|---|
| Control | 0 | 0 | 0 | 0 |
| Carrier low | 0 | 0.0627 | 0.418 | 0.4807 |
| Carrier high | 0 | 0.1254 | 0.836 | 0.9614 |
| $5 \times 10^9$ conidia/m² | 0.0209 | 0 | 0 | 0.0209 |
| $1 \times 10^{10}$ conidia/m² | 0.0418 | 0 | 0 | 0.0418 |
| $5 \times 10^9$ conidia/m² 1:3:20 | 0.0209 | 0.0627 | 0.418 | 0.5016 |
| $5 \times 10^9$ conidia/m² 1:6:40 | 0.0209 | 0.1254 | 0.836 | 0.9823 |
| $1 \times 10^{10}$ conidia/m² 1:3:20 | 0.0418 | 0.1254 | 0.836 | 1.0032 |

4.2 Addition of Insects

Insects were counted in the laboratory, transported in vials and released into the steel rings 24 hours after treatment. Both species were present within each of the steel rings and 50 insects of each species were used in each replicate. The refuge containing kibbled wheat was added to the arena approximately one hour after the introduction of the insects.

4.3 Assessment of Insects

Insect mortality was assessed after 7 days. Insects were collected from the rings into labelled glass tubes with the aid of a battery operated suction device. Refuges were removed from the rings and placed in labelled self-seal plastic bags. The numbers of live and dead insects of each species within each steel ring and the refuge was recorded.

4.4 Monitoring of Environmental Conditions

Temperature and humidity were monitored using Tinytag dataloggers (TGP 1500, Gemini Dataloggers Ltd, UK) (OPA0/AppEnt 002 and 003) located in two positions around the arenas. Lights within the store were switched on during treatment and assessments, but remained off at all other times.

4.5 Statistical Analysis

The difference in mortality between treatments was analysed by a generalized linear model (GLM) with a logit link function. Post-hoc tests were used to test for differences between the treatments by comparison of the least significant difference for the treatments. When treatment mortalities were 0% or 100% a least significant difference value could not be obtained and post-hoc comparisons based on the least significant difference were therefore not possible for these treatments.

5. Results

5.1 Environmental Conditions

The average temperature recorded in the grain store throughout the trial was 15.0° C. with a minimum of 9.3° C. and a maximum of 19.2° C. The average humidity during the trial recorded using the Tinytag dataloggers was 77.6% with a minimum of 51.1% and a maximum of 95.6%.

5.2 Insect Mortality Data

There was a significant effect of treatment on the mortality of both beetle species tested after 7 days exposure (GLM $F_{7,36}=2.42$, $P=0.045$, $F_{7,36}=44.56$, $P<0.001$ and $F_{7,36}=88.61$, $P<0.001$ for *O. surinamensis* and *C. ferrugineus*, respectively) (Table 2).

The highest mortalities for *O. surinamensis* were seen in the treatments with IMI398548, Entostat® and talc (Table 2). The treatments with conidia and the higher amount of Entostat® and talc ($5\times10^9/m^2$ 6:40 and $1\times10^{10}/m^2$ 3:20) gave a significantly higher mortality than the treatment with the lower amount of Entostat® and talc ($5\times10^9/m^2$ 3:20) (P<0.05). Similarly, a significant difference (P<0.05) in mortality of *O. surinamensis* was observed between the carrier low and carrier high treatments, with a lower level of mortality observed with the lower amount of carrier (Table 1). Treatments with the conidia alone were not significantly different to the control (P>0.05, Table 2).

The highest mortalities for *C. ferrugineus* were seen in the treatments with IMI398548, Entostat® and talc (Table 2). These treatments gave significantly greater mortality than the control and treatments with the conidia alone (P<0.05, Table 2). The carrier alone (Entostat® and talc) also gave significantly greater mortality than the control and conidia only treatments. A significant difference (P<0.05) in mortality of *C. ferrugineus* was observed between the carrier low and carrier high treatments, with a lower level of mortality observed with the lower amount of carrier (Table 2).

TABLE 2

Derived mean % mortality of insects 7 days after exposure to different treatments. % mortality is expressed in terms of the number of insects recovered for each species. Figures in parentheses are the derived 95% confidence intervals.

|  | *O. surinamensis* | *C. ferrugineus* |
|---|---|---|
| Control | 3.7a | 2.1a |
|  | (0.9, 14.0) | (0.4, 9.5) |
| Carrier low | 35.2b | 70.9b |
|  | (24.5, 47.7) | (60.5, 79.4) |
| Carrier high | 53.8c | 88.2c |
|  | (41.4, 65.8) | (79.3, 93.6) |
| $5 \times 10^9/m^2$ | 5.1a | 10.5a |
|  | (1.7, 13.9) | (5.5, 19.2) |
| $1 \times 10^{10}/m^2$ | 10.0a | 5.7a |
|  | (6.1, 22.4) | (2.4, 13.0) |
| $5 \times 10^9/m^2$ 6:40 | 93.6d, e | 100 |
|  | (82.1, 97.9) |  |
| $5 \times 10^9/m^2$ 3:20 | 80.2d | 97.6d |
|  | (69.1, 88.1) | (91.5, 99.3) |
| $1 \times 10^{10}/m^2$ 3:20 | 95.6e | 99.5c, d |
|  | (85.1, 98.8) | (88.7, 99.9) |

In each column means followed by the same letter are not significantly different (GLM; P > 0.05)

6. Conclusions

High levels of mortality (80-100%) were observed for *O. surinamensis* and *C. ferrugineus* in treatments with *B. bassiana* IMI398548, Entostat® and talc after 7 days exposure in treated arenas. For *O. surinamensis* the mortality observed in the *B. bassiana* IMI398548, Entostat® and talc treatments was greater than the additive mortality of the conidia only and carrier only treatments.

The Entostat® and talc carrier alone resulted in significant levels of mortality for *O. surinamensis* and *C. ferrugineus* compared with the control and conidia only treatments. The greater amount of the carrier gave the higher level of mortality.

Experiment 5

Field Scale Efficacy Testing of *Beauveria bassiana* Formulations Against Stored Grain Pests Summary A powder formulation of a biopesticide based on an isolate (IMI398548) of the entomopathogenic fungus *Beauveria bassiana*, which is active against stored grain pests, was tested in an on-farm grain store facility. The treatment was applied to the floor of two empty grain silos and then target beetle pests (*Oryzaephilus surinamensis* and *Cryptolestes ferrugineus*) were introduced to discrete arenas installed in the silos and monitored over time to measure the effects of the treatment on insect mortality. Mortality was compared to two grain silos that were split so that half received no treatment (untreated controls) and half received kaolin only (vehicle control). There was one outdoor and one indoor (inside a barn) silo for each treatment group. The trial was done in the autumn (September/October). Efficacy was determined by comparing the % total mortality of each species in the treated outdoor or indoor silo with the % total mortality of each species in the untreated control outdoor or indoor silo at each monitoring point using the Schneider-Orelli formula (Püntener, 1981 Manual for field trials in plant protection second edition. Agricultural Division, Ciba-Geigy Limited.).

The % efficacy in indoor and outdoor treated silos at each time point and for each species after adjustment for control mortality is given in the table below. Efficacy was very high (>90% death due to treatment) for the two species within 14 d post treatment.

|  |  |  | *O. surinamensis* | *C. ferrugineus* |
|---|---|---|---|---|
| Adjusted by untreated control | 7 days | Indoor | 51.58 | 76.83 |
|  |  | Outd'r | 5.34 | 61.14 |
|  | 14 days | Indoor | 100 | 99.05 |
|  |  | Outd'r | 100 | 97.69 |
| Adjusted by vehicle control | 7 days | Indoor | 42.86 | 71.16 |
|  |  | Outd'r | 0 | 36.16 |
|  | 14 days | Indoor | 100 | 97.82 |
|  |  | Outd'r | 100 | 90.93 |

In conclusion, under the conditions of this trial the biopesticide showed a high level of efficacy for the two target species.

Objective

To determine the efficacy of a dry powder formulation of *Beauveria bassiana* strain IMI398548 against stored product pest species.

Introduction

The purpose of this study was to examine the efficacy of a powder formulation of a biopesticide based on an isolate (IMI398548) of the entomopathogenic fungus *Beauveria bassiana* against stored grain pests under realistic field conditions.

This trial used realistic pest control operator (PCO) application equipment for applying the product to the whole floor of grain silos. This trial included a vehicle control treatment for the kaolin, monitoring mortality at 7 and 14 days and by testing the spore concentration at a low target rate ($5\times10^9$ total conidia per $m^2$). We aimed for a minimum deposition of $1\times10^9$ CFU/$m^2$.

Twenty-four hours following treatment, sample groups of grain beetles *Oryzaephilus surinamensis* (saw-toothed grain beetle) and *Cryptolestes ferrugineus* (rust-red grain beetle) were added to discrete arenas within the treated areas and monitored over time for mortality.

1. Test Item Details

Test item type: Dry powder formulation containing conidia of *Beauveria bassiana* strain IMI398548, Sylvan batch: 2112003 (CABI batch code: 142/12; FERA batch code TA 2672).
Test item contents: Fungus, Entostat® and Kaolin
Test item rate: $5 \times 10^9$ total conidia/m² (aiming for minimum $1 \times 10^9$ CFU/m²) Batch 2112003 contains $5.25 \times 10^{10}$ conidia/g (calculated at CABI) so we needed to apply 0.095 g of the dry spores per m². Entostat®, 0.768 g/m² and kaolin=5.120 g/m².
Supplier: IMI398548 was supplied by CABI of Bakeham Lane, Egham, Surrey, TW20 9TY). The kaolin is opal omega grade sourced from Goonvean Ltd (St Stephen, St Austell, Cornwall, United Kingdom, PL26 7QF). The Entostat® was manufactured at Exosect (batch W1307). The formulations were prepared at CABI using calibrated balance equipment, mixed thoroughly and sealed in a foil sachet.

2. Test Sites

The trial included four cylindrical grain storage silos. All of the silos had metal corrugated walls and solid concrete floors with side access through hatches or doorways. Two of the silos were located inside a barn (5 and 6) and were 3.6 m diameter and two were located outside (7 and 8) and were 5.7 m in diameter.

Insects were cultured and supplied by the invertebrate supply unit at FERA. Mortality counts were done at the FERA site.

The formulation was mixed at the CABI site. Calibration and validation work was also carried out at CABI.

3. Methodology 8.1. Experimental Design

There were four silos available for treatment, two inside a barn and two outside. One indoor silo (6) and one outdoor silo (7) were used for control treatments and the remaining two silos (5 and 8) were treated with the fungal formulation. Forty stainless steel arenas to contain the insects were present in each silo. In the control silos twenty of the arenas were covered over before treatment (so they could be kept as untreated controls and the carrier powder kaolin was applied to the whole silo. Insects were introduced to twenty of the arenas in the treated silos and all forty of the arenas in the control silos one day after the treatment applications. Insects were collected from ten of the untreated control arenas, vehicle control arenas and treated arenas after 7 d and the remaining arenas after 14 d. The insects were subjected to mortality checks. The trial period extended over a 2 week period.

8.2 Study Schedule

| Date | | Activity |
|---|---|---|
| 25/09/2012 | - D0 | Vacuum silos, cover untreated control arenas, apply kaolin and test item treatments |
| 26/09/2012 | - D1 | Uncover untreated control arenas, introduce insects and refuges to all arenas, cover all arenas with mesh, set-up data loggers |
| 03/10/2012 | - D8 | Collect insects from ten arenas in each treatment group |
| 04/10/2012 | - D9 | FERA count live and dead insects |
| 10/10/2012 | - D15 | Collect insects from remaining ten arenas in each treatment group, collect data loggers |
| 11/10/2012 | - D16 | FERA count live and dead insects |
| 30/10/2012 | | Trial clean-up |

8.3 Site Preparation

Before trial commencement the treated grain silos were vacuumed using a Numatic HZQ200-2 Hazardous Dust Vacuum Cleaner. The arenas were checked and thoroughly vacuumed to remove any remaining insects or treatment powder from previous trial work.

8.4 Arena Installation

Forty arenas in silos 6 and 7 (control silos) and twenty arenas in silos 5 and 8 (treatment silos) were used in this trial. The arenas were already in place on top of concrete paving flags (Marshalls FL1200600; 60×60 cm), four arenas per flag (ten flags per silo) in a 2×2 arrangement. Two arenas on each flag in silos 5 and 8 were not used. The arenas were made from stainless steel rings (Instant Fabrications Ltd, Chandlers Ford, Hants, UK; 20 cm diameter, 5 cm deep, 0.9 mm thick). The inside surfaces of the arenas were coated with Fluon (Blades Biological, UK) to prevent escape of the insects. The arenas were sealed to the concrete flag using aquarium sealant (Geocel Aquaria Aquarium Sealant: Sealants and Tools Direct Ltd) so that insects could not get underneath. A covering made from fine mesh material and held down with an elastic band was placed over each arena after insect introduction.

In silos 6 and 7 the arenas in blocks 3, 4, 5, 6 and 10 were covered over with clingfilm and taped down before treatment. These were the untreated controls and were covered to protect them from kaolin powder deposition. In silos 5 and 8 only two arenas, A and B, were used; A was sampled at 7 d and B at 14 d. In silos 6 and 7, A and B were sampled at 7 d and C and D at 14 d. Within blocks the codes were randomly assigned to the arenas using a table of random numbers.

8.5 Equipment Calibration

Application of the formulations and carrier powders were made using B&D Mini DustR applicators (Killgerm), one per silo. A calibration for the applicator was made.

The nature of the pump mechanism meant that there may have been variations in the amount of powder applied from each pump, thus a standard position was utilised when applying and calibrating. The applicator was held at a 45° angle with the application nozzle in the lowest position nearest to the floor. This ensured the feeder tube inside the powder chamber was covered with the maximum amount of powder at all times, thus minimizing variance in application rates. To ensure an even application, the powder applicator was moved in an 'arc' motion by the applicator with each puff. This was shown to be the most effective way to ensure even coverage during powder room trials at CABI facilities.

The applicator calibration results showed that the amount of powder per puff dropped as the powder applicator emptied, thus to ensure an even spread of powder the standardised pattern of application involved covering the entire floor of the silo in less than 10 puffs, then repeating this standard pattern. This ensured a more even application of powder than if the applicator had systematically covered the floor of the silo once until the powder applicator was empty.

8.6 Environmental Data Collection

Mean, max and min daily temperature and humidity readings for each grain silo were recorded from the day of insect introduction. Calibrated Lascar temperature and humidity loggers (model EL-USB-2) were positioned next to block 9 in each silo. Readings were collected every 60 min. The data was downloaded and analysed using Lascar software.

8.7 Application of Treatments

A separate applicator was used for each treatment (four in total: two test treatments and two vehicle control treatments).

The applications were made from the far side of the silo (opposite the entry) from applicator height with the nozzle directed downwards at a 45° angle in a standardized pattern, repeated until the applicator was empty. Treatment using kaolin only were made in silos 6 and 7 to the whole floor also, starting from the far side again. Only arenas in blocks 1, 2, 7, 8 and 9 received the carrier treatment—the other arenas were covered over with clingfilm so that they could be used for the untreated controls.

Before treatment the hatches of the outdoor silos were sealed shut. The indoor silos have doorways and the doors have been removed so the silos were sealed closed with polythene sheeting, cardboard and duct tape. Any ventilation pipes or holes in silos were covered with polythene sheeting and duct tape.

8.8 Insect Application and Monitoring

Two species of insect were tested: *Oryzaephilus surinamensis* strain Tram (saw-toothed grain beetle), and *Cryptolestes ferrugineus* strain Stow (rust-red grain beetle). Insects were of mixed age and sex. Insects were provided by the Invertebrate Supply Unit at FERA and reared according to FERA Standard Operating Procedures (ISU/018, ISU/023, ISU/025, ISU/026, ISU/034).

Insects were added 24 h after application of the treatments. In silos 6 and 7 (controls) each species was added to all of the arenas. In silos 5 and 8 only arenas A and B received insects. Each arena contained twenty of each species. A refuge made from a piece of electrical conduit (25×16×100 mm), containing kibbled wheat to provide food for the insects, was placed in the centre of each arena approximately 30 min before introduction of the insects.

Insects were collected at 7 or 14 d using battery operated pooters and transferred to glass vials. Refuges were removed from the rings and emptied into labeled zip-lock bags. The vials and bags were boxed and couriered overnight to FERA for counting.

8.9 Data Analysis

An adjustment for control mortality to the mean mortalities for each insect species in each treatment silo at each time point was calculated and is presented.

4. Results 9.1. Environmental Conditions

Conditions within the silos were quite different between the indoor and outdoor silos, with temperature and humidity fluctuating to a much greater degree in the outdoor silos; probably due to exposure to sun and lack of insulation outside (Table 1). Temperature minimums and maximums were lower and higher respectively in outdoor silos. The mean temperatures and humidity however were similar between indoor and outdoor silos. Conditions were also similar between silos 5 and 6 (indoor) and between 7 and 8 (outdoor).

9.2. Insect Survival

When the collected insects were being checked for mortality some of them were missing. It seemed unlikely that they had been able to climb out but in some arenas, due to the slight uneven surface, there was sufficient gap under the steel rings to allow some of the smaller beetles to take refuge and avoid being collected into the pooter. Because fewer than 10 beetles from one species were occasionally collected, and the arenas are not true replicates but samples, the total mortality in the silo from all arenas was calculated, rather than the mean mortality per arena.

Mortality in the untreated control arenas was notable at each time point for *O. surinamensis* (10-20%) and *C. ferrugineus* (10-30%), particularly in silo 7 where conditions were warmer and fluctuated to a greater degree. This could be attributed to the fact that the insects are laboratory reared and used to constant controlled conditions. There was no acclimation period because conditions at the site were variable so they may not have been able to adapt to such an abrupt change. An additional possibility is that the warm conditions caused volatilisation of toxic residues (confirmed to be present during pre-trial work) from the surfaces of the store so that even though insects were not in physical contact with the floor of the silo, they were still exposed to low levels of volatile compounds that could have affected their survival.

Survival of *O. surinamensis* and *C. ferrugineus* did seem to be affected by the carrier powders as mortality was greater than the untreated controls (27-60% and 28-82% respectively), particularly in Silo 7 where temperatures were warmer during the day.

Although some mortality may be attributed to the carrier powder kaolin, mortality in arenas which received the full formulation treatment experienced the highest levels of mortality. This would seem to indicate that the combination of *B. bassiana* isolate IMI398548 and kaolin with Entostat® provided the best level of control. Apart from lower than expected mortality (24%) in the outdoor treated silo at day 7, the mortality of *O. surinamensis* exposed to treatment was high (58% at day 7 in silo 5 and 100% in both silos at day 14). Mortality of *C. ferrugineus* was also high, even after just 7 days (7 d: 72-79% and 14 d: >98%).

The % efficacy in indoor and outdoor silos at each time point and for each species was calculated using the untreated control mortality and the vehicle control mortality with Schneider-Orelli's formula (Pintener, 1981 Manual for field trials in plant protection second edition. Agricultural Division, Ciba-Geigy Limited.), which adjusts for control mortality (see Table 2). Because the carrier kaolin caused some mortality the adjusted % efficacy using these figures are lower. To examine the overall effect of the formulation on the insects it is best to examine the % efficacy adjusted by the untreated controls. To understand the benefit of the fungus in the formulation it is best to examine the % efficacy adjusted by the vehicle control mortality.

5. Discussion

This trial is a series of trials designed to assess the mortality of insects exposed to a novel biopesticide treatment in grain storage silos. Insects were collected after 7 and 14 d and the concentration of spores added to the formulation was as stated above. The decision to check mortality at 7 d was beneficial as we were able to show that mortality of *O. surinamensis* was 20-60% and of *C. ferrugineus* was 80-90% in treatment silos. Clearly some mortality may be attributable to factors other than the treatment because mortality in the untreated controls was between 10-30% for these two species at 7 d. This may be largely attributable to the shock of being introduced to the arenas since untreated control mortality did not rise noticeably between 7 and 14 d.

The environmental conditions in the silos were suitable for both insect survival and fungal germination. Temperatures did not drop below 5° C. and did not rise above 22° C. The isolate survives well in a broad range of temperatures. High humidity (60-90% RH) will have aided the initial germination of the fungus, although this isolate has lower requirements for water activity than other *B. bassiana* isolates.

For a biological treatment the % efficacy achieved was high for *C. ferrugineus* after only 7 d, particularly in the indoor silo, and very high (>90%) after 14 d. For *O. surinamensis* the % efficacy was low in outdoor silos after 7 d but notable in the indoor silo (>50%). By 14 d the % efficacy for *O. surinamensis* was exceptional at 100% in both indoor and outdoor silos. We conclude that the efficacy for the two species *O. surinamensis* and *C. ferrugineus* after only 14 d post treatment was very good.

Tables

TABLE 1

Max, min and mean temperature and humidity in each of the silos during the trial

| Silo | | | Temperature | | | % RH | | |
|---|---|---|---|---|---|---|---|---|
| | | | Max | Min | Mean | Max | Min | Mean |
| 5 | treated | indoor | 15.00 | 9.00 | 13.02 | 89.00 | 71.50 | 82.13 |
| 6 | untreated | indoor | 15.00 | 9.00 | 12.92 | 89.00 | 71.00 | 82.34 |
| 7 | untreated | outdoor | 21.00 | 4.50 | 12.99 | 92.00 | 54.50 | 82.56 |
| 8 | treated | outdoor | 20.50 | 4.50 | 12.96 | 93.50 | 61.50 | 84.96 |

TABLE 2

% efficacy in indoor and outdoor treated silos at each time point and for each species after adjustment for untreated control and vehicle control mortality using Schneider-Orelli's formula (Püntener, 1981)

| | | | *O. surinamensis* | *C. ferrugineus* |
|---|---|---|---|---|
| Adjusted | 7 days | Indoor | 51.58 | 76.83 |
| by | | Outd'r | 5.34 | 61.14 |
| untreated | 14 days | Indoor | 100 | 99.05 |
| control | | Outd'r | 100 | 97.69 |
| Adjusted | 7 days | Indoor | 42.86 | 71.16 |
| by | | Outd'r | 0 | 36.16 |
| vehicle | 14 days | Indoor | 100 | 97.82 |
| control | | Outd'r | 100 | 90.93 |

In the context of this specification the term "electret particles" is to be understood as embracing electrostatically charged particles, including (but not restricted to) wax particles produced by the methods hereinbefore described.

The invention claimed is:

1. A dry powder formulation comprising:
   i) spores of an entomopathogenic fungus that has activity against arthropods that infest dry commodity storage areas, wherein the spores are present in an amount of 2 to 5% w/w of the formulation;
   ii) mineral-based particles of an industrial mineral in an amount of 80 to 88% w/w of the formulation and having a volume mean diameter of ≥5 μm; and
   iii) electret particles, different from said mineral-based particles, in an amount of 10 to 15% w/w of the formulation.

2. The formulation of claim 1, wherein the spores of i) are present in an amount of 2 to 4.5% w/w; the mineral-based particles of ii) are present in an amount of 82.5 to 87% w/w; and the electret particles of iii) are present in an amount of 11 to 13% w/w of the formulation.

3. The formulation of claim 1, wherein the spores of i) are present in an amount of 2.10 to 4.17% w/w; the mineral-based particles of ii) are present in an amount of 83.0 to 85.0% w/w and the electret particles of iii) are present in an amount of 12.5 to 12.80% w/w of the formulation.

4. The formulation of claim 1, wherein the spores are present in an amount of at least $1 \times 10^9$ CFU/gram dry weight.

5. The formulation of claim 1, wherein the spores are present in an amount of at least $1 \times 10^{10}$ CFU/gram dry weight.

6. The formulation of claim 1, wherein the spores are present in an amount of at least $1 \times 10^{11}$ CFU/gram dry weight.

7. The formulation of claim 1, wherein the industrial mineral is selected from clays, sand, gravel, diatomite, diatomaceous earth, kaolin, bentonite, silica, barite, gypsum, and talc or a mixture of two or more thereof.

8. The formulation of claim 1, wherein the industrial mineral is selected from kaolin and talc or a mixture thereof.

9. The formulation of claim 1, wherein the arthropods comprise *Sitophilus oryzae*, *Sitophilus granarius*, *Sitophilus zeamais*, *Rhyzopertha dominica*, *Ahasverus advena*, *Oryzaephilus surinamensis*, *Prostephanus truncatus* and *Cryptolestes ferrugineus*.

10. The formulation of claim 1, wherein the arthropods comprise *Oryzaephilus surinamensis*, *Sitophilus granarius* and *Cryptolestes ferrugineus*.

11. A method of using the formulation of claim 1, comprising controlling arthropod infestation in a dry commodity storage area (facility) with the formulation of claim 1.

12. A method of using the formulation of claim 1, comprising controlling, with the formulation of claim 1, arthropod infestation within and/or on a dry commodity selected from whole grains and seeds for sowing, whole grains selected from wheat, rice, rye, oats, barley and corn for use as food and/or in the manufacture of processed foods, pulses, beans, lentils and products made therefrom from or made with dried commodities, dry processed goods including pasta, grain flours, couscous, cereals, dried herbs, breakfast cereals, semolinas, breads, nuts (ground, flaked and/or whole nuts), snacking food selected from sweet and savoury biscuits, potato crisps, vegetable crisps, pretzels, dried wafers, domestic livestock feed, timber lumber, planking, articles made of timber including roof scaffolding for buildings, panelling, doors and door frames, lintels, skirting boards, hardboards, plywoods, furniture, and woodchips.

13. A method of controlling dry commodity arthropod infestation in a dry commodity storage area, wherein the formulation of claim 1 is presented to the surfaces of a dry commodity storage area by
   i) collecting the dry powder formulation in a dusting apparatus; and
   ii) releasing the said dry powder formulation from the said dusting apparatus and into the said dry commodity storage area.

14. A method of controlling dry commodity arthropod infestation in a dry commodity storage area, wherein the formulation of claim 1 is presented to the surfaces of a dry commodity storage area.

15. A dry powder formulation comprising:
   i) spores of an entomopathogenic fungus that has activity against an arthropod selected from *Oryzaephilus suri-*

*namensis, Sitophilus granarius* and *Cryptolestes ferrugineus*, wherein the spores are present in an amount of 2 to 5% w/w of the formulation, and in an amount of at least $1\times10^{10}$ CFU/gram dry weight;
ii) mineral-based particles of an industrial mineral selected from kaolin, talc, and a mixture of kaolin and talc, in an amount of 80 to 88% w/w of the formulation and having a volume mean diameter of ≥5 μm; and
iii) electret particles, different from said mineral-based particles, in an amount of 10 to 15% w/w of the formulation.

16. A method of producing a dry powder formulation comprising:
    i) spores of an entomopathogenic fungus comprising *Beauveria bassiana* that has activity against arthropods that infest dry commodity storage areas, wherein the spores are present in an amount of 2 to 5% w/w of the formulation;
    ii) mineral-based particles of an industrial mineral in an amount of 80 to 88% w/w of the formulation and having a volume mean diameter of ≥5 μm; and
    iii) electret particles, different from said mineral-based particles, in an amount of 10 to 15% w/w of the formulation, comprising the steps of
    i) micronising dry electret particles;
    ii) admixing dry spores of the entomopathogenic fungus comprising *Beauveria bassiana* with said electret particles, wherein the spores are present in an amount of 2 to 5% w/w of the formulation and the electret particles are present in an amount of 10 to 15% w/w of the formulation; and
    iii) admixing dry industrial mineral earth particles, having a volume mean diameter of ≥5 μm in an amount of 80 to 88% w/w of the formulation, with the product of step ii).

17. A dry powder formulation, comprising:
    i) spores of an entomopathogenic fungus comprising *Beauveria bassiana* that has activity against arthropods that infest dry commodity storage areas, wherein the spores are present in an amount of 2 to 5% w/w of the formulation;
    ii) mineral-based particles of an industrial mineral in an amount of 80 to 88% w/w of the formulation and having a volume mean diameter of ≥5 μm; and
    iii) electret particles in an amount of 10 to 15% w/w of the formulation, wherein the formulation is produced by the method of claim 16.

* * * * *